United States Patent [19]

Wong

[11] Patent Number: 5,164,188

[45] Date of Patent: Nov. 17, 1992

[54] BIODEGRADABLE OCULAR IMPLANTS

[75] Inventor: Vernon G. Wong, Rockville, Md.

[73] Assignee: Visionex, Inc., Sunnyvale, Calif.

[21] Appl. No.: 440,344

[22] Filed: Nov. 22, 1989

[51] Int. Cl.$^5$ ............................................. A61F 2/14
[52] U.S. Cl. ................................ 424/428; 424/422; 424/423; 424/427; 424/484; 424/486; 514/912; 514/914
[58] Field of Search ............... 424/422, 423, 427, 428, 424/484, 486; 514/912, 914; 623/4

[56] References Cited

U.S. PATENT DOCUMENTS

| | | | |
|---|---|---|---|
| 3,870,791 | 3/1975 | Haddad et al. | 424/427 |
| 3,962,414 | 6/1976 | Michaels | 424/473 |
| 4,001,388 | 1/1977 | Shell | 424/438 |
| 4,052,505 | 10/1977 | Higuchi et al. | 424/427 |
| 4,057,619 | 11/1977 | Higuchi et al. | 424/427 |
| 4,186,184 | 1/1980 | Zaffaroni | 424/427 |
| 4,190,642 | 2/1980 | Gale et al. | 424/427 |
| 4,281,654 | 8/1981 | Shell et al. | 424/427 |
| 4,303,637 | 12/1981 | Shell et al. | 424/427 |
| 4,304,765 | 12/1981 | Shell et al. | 424/427 |
| 4,865,599 | 9/1989 | Chiou et al. | 424/427 |

FOREIGN PATENT DOCUMENTS

| | | |
|---|---|---|
| 339861 | 5/1985 | European Pat. Off. . |
| 0170540 | 5/1986 | European Pat. Off. . |
| 0330389 | 8/1989 | European Pat. Off. ............ 514/912 |

OTHER PUBLICATIONS

Matsumoto et al., "Effects of Various Irrigating Solutions of the Blood Aqueous Barrier of the Cannine Eye" Atarashii Ganka (1984) 1:129-131.

Liu et al., "Intravitreal Liposome' Encapsulated Trifluorothymidine in a Rapid Model" Opthalmology (1987) 94:1155-1158.

*Primary Examiner*—Thurman K. Page
*Assistant Examiner*—Carlos Azpuru
*Attorney, Agent, or Firm*—Bertram I. Rowland

[57] ABSTRACT

Encapsulated agents are employed for introduction into the suprachoroid of an eye for therapeutic purposes. The administration of drugs is controlled and maintained for long periods of time, while ensuring the substantial absence of significant levels outside the site of administration.

7 Claims, No Drawings

BIODEGRADABLE OCULAR IMPLANTS

INTRODUCTION

1. Technical Field

Biocompatible implants are provided for treatment of ocular diseases.

2. Background of the Invention

The eye is fundamentally one of the most important organs during life. Because of aging, diseases and other factors which can adversely affect vision, the ability to maintain the health of the eye becomes all important. A leading cause of blindness is the inability in the treatment of eye diseases to introduce drugs or therapeutic agents into the eye. Oral ingestion of a drug or injection of a drug at a site other than the eye does not provide effective levels of the drug specifically to the eye. On the other hand, when a drug is injected into the eye, it quickly washes out or is depleted from within the eye into the general circulation. From the therapeutic standpoint, this may be as difficult as giving no drug at all. Because of this inherent difficulty of delivering drugs into the eye, successful medical treatment of ocular diseases is inadequate.

The need for a solution is even more pressing in that the cause of a number of ocular diseases have now been identified and many are amenable to treatment if a proper mode of therapeutic delivery is available. It is therefore of great interest to develop modes of treatment which obviate the limitations of present modes of therapy.

3. Relevant Literature

U.S. application Ser. No. 136,402 discloses biocompatible implants for introducing into an anterior or posterior chamber of an eye for the treatment of an ocular condition.

Heller (1), Biodegradable Polymers in Controlled Drug Delivery, in: CRC Critical Reviews in Therapeutic Drug Carrier Systems, Vol. 1, CRC Press, Boca Raton, FL, 1987, pp 39-90, describes encapsulation for controlled drug delivery. See also, Heller (2), in: Hydrogels in Medicine and Pharmacy, N. A. Peppes ed., Vol. III, CRC Press, Boca Raton, FL, 1987, pp 137-149, describes bioerodible polymers. Heller, *J. of Controlled Release* (1985) 2:167-177; Leong et al., *BioMaterials* (1986) 7:364-371 describes polyanhydride microspheres. Jackanicz et al., *Contraception* (1973) 8:227; Yolles et al., in: Controlled Release of Biologically Active Agents, Tanquary et al. eds, Plenum Press, New York, NY, 1974, Chapter 3; Liu et al., *Opthamology* (1987) 94:1155-1159 and references cited therein report a study for the intravitreal use of liposomes for therapeutic treatment of eye disease. See also Cutright et al., *Oral Surgery, Oral Medicine, and Oral Pathology* (1974) 37:142 and Shindler et al., *Contemporary Topics in Polymer Science* (1977) 2:251289. Anderson et al., *Contraception* (1976) 13:375 and Miller et al., *J. Biomed. Materials Res.* (1977) 11:711, describe various properties of poly(dL-lactic acid). U.S. Pat. Nos. of interest include 3,416,530; 3,626,940; 3,828,777; 3,870,791; 3,916,899; 3,944,064; 3,962,414; 4,001,388; 4,052,505; 4,057,619; 4,164,559; 4,179,497; 4,186,184; 4,190,642; 4,281,654; 4,303,637; 4,304,765; 4,304,767; 4,439,198; 4,452,776; 4,474,751; 4,613,330; and 4,617,186.

SUMMARY OF THE INVENTION

Biocompatible, particularly biodegradable, implants are introduced into the suprachoroid of an eye to provide a therapeutically effective amount of an agent for treatment of an ocular condition. The implants are provided as plaques and/or microspheres or microcapsules for precise delivery of a specific agent to interior regions of an eye.

DESCRIPTION OF THE SPECIFIC EMBODIMENTS

Ocular conditions, diseases, tumors and disorders, are treated by introducing slow release agent-containing biocompatible implants directly into the suprachoroid of an eye, particularly a mammalian eye. The suprachoroid can be entered or exposed surgically and implants placed strategically in the exposed space in dimensions commensurate with the size and shape of the suprachoroid without migration of the implant from the insertion site. The implants, in the form of sheets or plaques, are formulated to include one or more agents which may be released over an extended period of time at a therapeutically effective dosage into the interior of an eye. In this manner, agents released from implants can reach the choroid, retina, and vitreous.

Diffusion can be further controlled so that delivery of various agents will be precise. For example, delivery of a specific agent to just the underlying choroid can be controlled by the concentration of the agent in the implant and the rate of release. By increasing the concentration and diffusion rate, the agent will diffuse into the vitreous or alternatively into the apposed retina. Thus, the agent can be made available to the site(s) where the agent is needed and will be maintained at an effective dosage, rather than rapidly being washed out, or as in the case of systemic administration, requiring greatly elevated levels of drug administration to the host to achieve an effective level in the eye.

Implants comprising the agent or agents of interest to be administered to an eye are generally encapsulated. The capsule, for the most part, will be a polymeric encapsulating agent. Material capable of being placed in a given area of the suprachoroid without migration, such as oxycel, gelatin, silicone, etc. can also be used. The compositions will be biocompatible, preferably biodegradable.

For the most part, the polymeric compositions will be organic esters or ethers, which when degraded result in physiologically acceptable degradation products, including the monomers. Anhydrides, amides, orthoesters or the like, by themselves or in combination with other monomers, may find use. The polymers may be addition or condensation polymers, particularly condensation polymers. The polymers may be crosslinked or non-cross-linked, usually not more than lightly cross-linked, generally less than 5%, usually less than 1%. For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen may be present as amide, cyano and amino. The polymers set forth in Heller (1), supra, may find use, and that disclosure is specifically incorporated herein by reference.

Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate, a slowly eroding polymer is achieved, while erosion is substantially enhanced with the lactate racemate.

Among the polysaccharides will be calcium alginate, and functionalized celluloses, particularly carboxymethylcellulose esters characterized by being water insoluble, a molecular weight of about 5 kD to 500 kD, etc. Other polymers of interest include polyvinyl alcohol, esters and ethers, which are biocompatible and may be biodegradable or soluble. For the most part, characteristics of the polymers will include biocompatibility, compatibility with the agent of interest, ease of encapsulation, a half-life in the physiological environment of at least 6 hrs, preferably greater than one day, no significant enhancement of the viscosity of the vitreous, water insoluble, and the like.

The biodegradable polymers which form the implants will desirably be subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, where the polymers may be employed as varying layers or mixed.

By employing a biodegradable polymer, particularly one where the biodegradation is relatively slow, the rate of release of the drug will be primarily diffusion controlled, depending upon the surrounding membrane or monolithic polymer structure, rather than breakdown of the particle. For the most part, the selected particles will have lifetimes at least equal to the desired period of administration, preferably at least twice the desired period of administration, and may have lifetimes of 5 to 10 times the desired period of administration. The period of administration will usually be at least 3 days, more usually at least 7 days, generally at least about 15 days and may be 20 days or more.

The particles may be substantially homogeneous as to composition and physical characteristics or heterogeneous. Thus, particles can be prepared where the center may be of one material and the surface have one or more layers of the same or different composition, where the layers may be cross-linked, of different molecular weight, different density or porosity, or the like. For example, the center could be a polylactate coated with a polylactatepolyglycolate copolymer, so as to enhance the rate of initial degradation. Most ratios of lactate to glycolate employed will be in the range of about 1:0-1. Alternatively, the center could be polyvinyl alcohol coated with polylactate, so that on degradation of the polylactate the center would dissolve and be rapidly washed out of the eye.

Any pharmacologically active agent for which sustained release is desirable may be employed including drugs, pharmaceutical agents, bacterial agents, etc. The agents will be capable of diffusion into the vitreous to be present at an effective dose. In this manner, drugs or pharmaceutical agents will be sufficiently soluble to be presented at pharmacologically effective doses. Pharmacologic agents which may find use may be found in U.S. Pat. Nos. 4,474,451, columns 4-6 and 4,327,725, columns 7-8, which disclosures are incorporated herein by reference.

Bacterial agents include acid fast bacilli, (BCG), *Corynebacterium parvum*, LPS, endotoxin etc. These agents induce an immune response enhancing immune attack of tumor cells. These agents are frequently used as immune adjuvants to enhance an immune response to an administered antigen. See Morton et al., *Surgery* (1970) 68:158-164; Nathanson, L., *Cancer Chemother. Rep.* (1973) 56:659-666; Pinsky et. al., *Proc. AACR* (1972) 13:21; and, Zhar et. al., *J. Nat'l Cancer Inst.* (1971) 46:831-839.

Drugs of particular interest include hydrocortisone (5 to 20 mcg as plasma level), gentamycin (6 to 10 mcg/ml in serum), 5-fluorouracil (-30 mg/kg body weight in serum), sorbinil, IL-2, TNF, Phakan-a (a component of glutathione), thiolathiopronin, Bendazac, acetylsalicylic acid, trifluorothymidine, interferon ($\alpha$, $\beta$ and Y), immune modulators, e.g., lymphokines, monokines, and growth factors, cytokines, anti-(growth factors), etc.

Other drugs of interest include anti-glaucoma drugs, such as the beta-blockers: timolol maleate, betaxolol and metipranolol; mitotics: pilocarpine, acetylcholine chloride, isoflurophate, demacarium bromide, echothiophate iodide, phospholine iodide, carbachol, and physostigimine; epinephrine and salts, such as dipivefrin hydrochloride; and dichlorphenamide, acetazolamide and methazolamide; anti-cataract and anti-diabetic retinopathy drugs, such as aldose reductase inhibitors: tolrestat, lisinopril, enalapril, and statil; thiol cross-linking drugs other than those considered previously; anti-cancer drugs, such as retinoic acid, methotrexate, adriamycin, bleomycin, triamcinolone, mitomycin, cis-platinum, vincristine, vinblastine, actinomycin-D, ara-c, bisantrene, CCNU, activated cytoxan, DTIC, HMM, melphalan, mithramycin, procarbazine, VM26, VP16, and tamoxifen; immune modulators, other than those indicated previously; anti-clotting agents, such as tissue plasminogen activator, urokinase, and streptokinase; anti-tissue damage agents, such as superoxide dismutase; proteins and nucleic acids, such as mono- and polyclonal antibodies, enyzmes, protein hormones and genes, gene fragments and plasmids; steroids, particularly anti-inflammatory or antifibrous drugs, such as cortisone, hydrocortisone, prednisolone, prednisone, dexamethasone, progesterone-like compounds, medrysone (HMS) and fluorometholone; non-steroidal anti-inflammatory drugs, such as ketrolac tromethamine, diclofenac sodium and suprofen; antibiotics, such as loridine (cephaloridine), chloramphenicol, clindamycin, amikacin, tobramycin, methicillin, lincomycin, oxycillin, penicillin, amphotericin B, polymyxin B, cephalosporin family, ampicillin, bacitracin, carbenicillin, cephololthin, colistin, erythromycin, streptomycin, neomycin, sulfacetamide, vancomycin, silver nitrate, sulfisoxazole diolamine, and tetracycline; other antipathogens, including anti-viral agents, such as idoxuridine, trifluorouridine, vidarabine (adenine arabinoside), acyclovir (acycloguanosine), gancyclovir, pyrimethamine, trisulfapyrimidine-2, clindamycin, nystatin, flucytosine, natamycin, miconazole and piperazine derivatives, e.g. diethylcarbamazine; cycloplegic and mydriatic agents, such as atropine, cyclogel, scopolamine, homatropine and mydriacyl.

Other agents include anticholinergics, anticoagulants, antifibrinolytic agents, antihistamines, antimalarials, antitoxins, chelating agents, hormones, immunosuppressives, thrombolytic agents, vitamins, salts, desensitizing agents, prostaglandins, amino acids, metabolites and antiallergenics.

The amount of agent employed in the implant will vary widely depending on the effective dosage required and rate of release. Usually the agent will be from about 1 to 80, more usually 20 to 40 weight percent of the implant.

Other agents may be employed in the formulation for a variety of purposes. In addition to the drug agent, buffering agents and preservatives may be employed. The water soluble preservatives include sodium bisulfite, sodium thiosulfate, ascorbate, benzalkonium chloride, chlorobutanol, thimerosal, phenylmercuric borate, parabens, benzyl alcohol and phenylethanol. These agents may be present in individual amounts of from about 0.001 to about 5% by weight and preferably about 0.01 to about 2%. Suitable water soluble buffering agents are alkali or alkaline earth, carbonates, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4 to 8. As such the buffering agent may be as much as 5% on a weight to weight basis of the total composition.

The size of the implants will range from about 0.5 mm×0.5 mm sheets to sheets of a size of one-quarter to one-half the sphere of the eye. The upper limit for the implant size will be determined by factors such as eye toleration for the implant, size limitations on insertion into the suprachoroid, ease of handling, etc. Sheets in the range of about 3–10 mm×5–10 mm with a thickness of about 0.25–1.0 mm are generally employed for ease of handling. The size and form of the implant can be used to control the rate of release, period of treatment, and drug concentration in the eye. In some situations mixtures of implants may be utilized employing the same or different pharmacological agents. In this way, in a single administration a course of drug treatment may be achieved, where the pattern of release may be greatly varied.

Various techniques may be employed to produce the implants. Useful techniques include solvent-evaporation methods, phase separation methods, interfacial methods and the like.

In preparing the polymeric encapsulated agents, for the most part solvent-evaporation methods will be employed. Towards this end, the preformed rate controlling polymer is dissolved in a volatile substantially water-immiscible solvent, such as chloroform, methylene chloride, or benzene. Sometimes, the water immiscible solvent will be modified with a small amount of a water-miscible organic cosolvent, particularly an oxygenated solvent, such as acetone, methanol, ethanol, etc. Usually, the water-miscible organic cosolvent will be less than about 40 vol %, usually less than about 25 vol %. The agent may then be added to the polymer-solvent solution. Depending upon the nature of the agent, one may have the agent dispersed in the viscous polymer-solvent mixture or a solid dispersion of drug particles, where the drug will have been pulverized to obtain a fine powder, usually a microfine powder particularly of a size of less than about 1 mM, usually less than about 0.5 mM, and may be about 0.5 µM or smaller.

The amount of polymer employed in the medium will vary with the size of the implant desired, whether additional coatings will be added, the viscosity of the solution, the solubility of the polymer and the like. Usually, the concentration of polymer will be in the range of 10 to 80 weight percent. The ratio of agent to polymer will vary with the desired rate of release, the amount of agent generally varying in the range of 1 to 80 weight percent of the polymer.

The dispersion or solution obtained above can be poured or layered onto a surface such as a petri plate. By variation of surface area in relationship to the volume of polymer solution, the layer can be made to conform to any desired dimensions including surface area and width.

A membrane coating is formed around the layered solution to provide an encapsulated implant for controlled, prolonged release of the active agent. To form the coating, an appropriate aqueous solution, generally water, is slowly poured over the surface. In this manner, polymerization results in a membrane surrounding the drug or agent. The resulting membrane bound plaques can be cut to any size for insertion into an eye. Alternatively, to produce sheets of a particular dimension, the solution can be layered into preformed molds and the surface polymerized. In this manner, plaques are ready for use without having to be cut to desired sizes.

The dispersion or solution can alternatively be added to a rapidly stirred aqueous solution comprising water and a dispersion agent, which may be a protective colloid. To form macromolecules, dispersing agents such as poly(vinyl alcohol) (1 to 5%) or nonagents, such ionic, detergents, such as Span detergents are employed.

The ratio of drug to polymer is adjusted to produce optimized compositions, since the final product will normally result in the initial ratio. By manipulating the initial bulk viscosity of the drug-polymer-solvent mixture and of the aqueous dispersing medium, the dissolved polymer agent/mixture may also be added to a rapidly stirred aqueous solution. In this instance the polymer mixture will coalesce in the absence of a dispersing agent, resulting in a large sheet or mass of encapsulation or macroencapsulation. Macroencapsulation can also be achieved when stirring of the aqueous solution during coacervation is slowed or stopped. Macrocapsules are then shaped into plaques for insertion into an eye.

Plaques may also be formed by mixing the agent with molten polymer at the appropriate temperature, for example for molten polylactic polymer, between 60 to 90° C. When cooled the resulting mixture can be cut or molded, as described above, into any shape or size for insertion into an eye.

The process may be carried out conveniently at room temperature, but cooling or heating may be employed in specific situations to optimize the process.

In order to define the potential drug-release behavior of the implants in vivo, a weighed sample of the implants may be added to a measured volume of a solution containing four parts by weight of ethanol and six parts by weight of deionized water. The mixture is maintained at 37° C. and stirred slowly to maintain the implants in suspension. The appearance of the dissolved drug as a function of time may be followed spectrophotometrically until the absorbance becomes constant or until greater than 90% of the drug has been released. The drug concentration after 1 h in the medium is indicative of the amount of free unencapsulated drug in the dose, while the time required for 90% drug to be released is related to the expected duration of action of the dose in vivo. As a general rule, one day of drug release in vitro is approximately equal to 35 days of release in vivo. While release may not be uniform, normally the release will be free of larger fluctuations from some average value which allows for a relatively uniform release.

The implants may be administered into the eye in a variety of ways, including surgical means, injection, trocar, etc.

Surgical procedures, such as those known in the art, will be necessary to position large macrocapsules or plaques into the suprachoroid. For example, the implants can be inserted through a sclerotomy. In this instance, the sclera is cut to expose the suprachoroid. An implant is then inserted into the suprachoroid on either side of the incision. Or, a full-thickness scleral trap-door can be fashioned to expose the suprachoroid. An implant is then inserted into the suprachoroid. The scleral flap is sewn back into place to secure the implant. Alternatively, where the implant is to be positioned over the pars plana a flap is cut over the pars planar to remove the eye coat. A hole is made through the pars plana to communicate with the vitreous. Thus, the implant can be positioned in the pars plana and the flap of eye coat sown back into place. If the implant is positioned over the pars plana of the eye, drug will diffuse readily into the vitreous and into the intraocular structure. This is made possible because of the relative avascular nature of the pars plana.

The following examples are offered by way of illustration and not by way of limitation.

EXPERIMENTAL

Choroidal Implantation

Brown-Pierce (BP) carcinoma was implanted into the choroidal bed in one eye of each of six rabbits. The tumor grew into appropriate size, simulating that of the human, within 3 to 6 weeks. Tubercle bacilli (BCG - Bacille Calmette-Guerin) $1.0 \times 10^8$ was thoroughly mixed in 2 ml of molten polylactic polymer between 60° to 90° C. The melted mixture was then plated and cooled at room temperature to a thickness of 0.5 to 0.75 mm. A 4 to 5 mm disc (or plaque) was trephined from the hardened polylactate-BCG mixture. This disc or plaque wa then surgically implanted into the base of the tumor. After 7 to 10 days, the size of the tumor did not increase and the tumor became discolored. Over the ensuing 6 to 8 weeks tumor resorption continued and total resolution was complete by 3 months.

Tumor reimplantation in each of the six animals in the anterior chamber, in the choroidal bed of the control eye, and infusion of $1 \times 10^7$ tumor cells intravenously was followed by no tumor growth and there was no animal morbidity. At necropsy, tumor infiltration was not observed in all major organs, including the once tumor bearing eye.

In each of six control animals, the impregnated polylactic plaques induced a corresponding local chorioretinitis with no further disturbance of the eye. On implantation of The Brown-Pierce tumor into the anterior chamber (AC) and choroidal bed, tumor growth was observed. Each of the animals succumbed to generalized metastases on subsequent infusion of $1 \times 10^7$ malignant cells.

Acid-fast bacilli (tbc) incorporated into polylactic acid eradicated intraocular BP tumor and established a specific immunity both locally and systemically against the implanted intraocular tumor.

Polylactic acid incorporated *Corynebacterium parvum* (*C. parvum*) gave identical results as those observed with polylactic acid incorporated acid-fast bacilli. 100 mg of *C. parvum* was mixed with 1000 mg of polylactate solubilized in 2 ml chloroform and 0.25 ml of ethanol. The mixture was plated over a thin layer of water to approximately 0.5 mm in thickness before a disc or plaque of 5 mm was trephined from the center of the plated mixture. Coascervation was completed by covering the plated mixture with additional water for 8 hours under low vacuum. Water was discarded and the preparation was dried in vacuum and desiccation for an additional 24 hrs. The trephined disc of coascervated *C. parvum* was surgically implanted into the base of the tumor. In each instance, tbc and *C. parvum* with polylactic acid demonstrated specific anti-tumor activity, adjuvant and immunizing properties.

Vincristine and VX2 Adenocarcinoma

Both eyes of six rabbits were implanted in the choroidal bed with VX2 adenocarcinoma. Intraocular growth simulated those of the human eye. Without treatment the tumor will grow uncontrolled with distant metastasis and ocular rupture.

Vincristine, a vinca alkaloid, known to be effective against VX2 adenocarcinoma with an in vitro IC50 in the range of 0.002–0.003 µg/ml, was incorporated with polyactic acid. When VX2 was implanted and grew to an appropriate intraocular size of $6.5\ mm \times 6.5\ mm$ (range 5.5 to 7.5 mm), polylactate incorporated vincristine was imbedded at the base of the choroidal tumor. 10 mg of Vincristine was mixed with approximately 500 mg of molten polylactate polymer and poured into a thin layer of 0.4 to 0.5 mm thickness and cooled in room temperature overnight. A disc of 5 mm was trephined from the hardened mixture and placed into the base of the choroidal tumor. The control eye received only the lactic acid polymer. Tumor regression was noted clinically within 6 to 9 days and complete resolution by 7 to 9 weeks. Tumor in the untreated control eye grew and caused tumor extension with subsequent rupture of the globe.

Pars Plana Drug Delivery

The exposure to the vitreous base at the pars plana could be performed by fashioning a full thickness scleral flap or by trephining through the bed of the sclera within a lamellar trap door. Encapsulated microspheres can be placed through the trephined hole(s) and thus into the vitreous base. Alternatively, polylactate incorporated drug formed into plaques of 3 to $5 \times 7$ to 9 mm with a thickness of 0.25 to 1.0 mm are placed within the trap door and held in place with closure of the scleral flap.

Drug Diffusion by Way of Pars Plana

One eye of each of six rabbits was implanted at the pars plana with methotrexate (MTX)-lactic acid microspheres and in one eye of another six rabbits with hydrocortisone acetate-lactic acid microspheres.

A 40% (by weight) mixture of MTX and hydrocortisone with polylactate polymer were solubilized in chloroform and ethanol (Table 1). Coascervation into microcapsules took place in 500 ml of a 5% polyvinyl alcohol aqueous solution with moderate to high speed stirring. Evaporation was performed under light vacuum with constant stirring for an additional 8 hrs. The resulting microspheres measuring 0.1 to 0.5 mm were selected and dried in vacuum for an additional 24 to 48 hours. Approximately 25 microcapsules were implanted at the pars plana.

A 40% (by weight) of MTX and hydrocortisone and polylactate polymer were mixed under moltened conditions (Table 2). The resulting mixture was plated into a thin layer of approximately 0.4 to 0.5 mm in thickness and cooled overnight at room temperature. A plaque measuring approximately 3×4 mm was fashioned from the layer and was surgically placed into the pars plana.

Results of the experiments were as follows:

TABLE 1

| # | Drug μg/ml | Assay | Time wks | RE AC | RE PC | LE AC | LE PC |
|---|---|---|---|---|---|---|---|
| 1* | MTX | EMIT | 1 | — | 0.8 | — | 0 |
| 2* | " | " | 2 | — | 1.2 | — | 0 |
| 3* | " | " | 3 | — | 1.4 | — | 0 |
| 4* | " | " | 4 | — | 0.7 | — | 0 |
| 5* | " | " | 5 | — | 1.0 | — | 0 |
| 6* | " | " | 6 | — | 0.9 | — | 0 |
| 7* | Hydro-cortisone | HPLC | 1 | — | 0 | — | 1.3 |
| 8* | Hydro-cortisone | " | 2 | — | 0 | — | 2.0 |
| 9* | Hydro-cortisone | " | 3 | — | 0 | — | 2.4 |
| 10* | Hydro-cortisone | " | 4 | — | 0 | — | 1.1 |
| 11* | Hydro-cortisone | " | 5 | — | 0 | — | 0.9 |
| 12* | Hydro-cortisone | " | 6 | — | 0 | — | 2.0 |

\# = Animal = Rabbit
\* = Microcapsule in pars plana
+ = Plaque in pars plana
RE = Right Eye
LE = Left Eye
AC = Anterior Chamber
PC = Posterior Chamber

TABLE 2

Plaques of MTX and hydrocortisone were given to one eye of each of 3 animals at the pars plana and over the vitreous base following scleral resection. The results are given in Table 2.

| # | Drug μg/ml | Assay | Time mos | RE AC | RE PC | LE AC | LE PC |
|---|---|---|---|---|---|---|---|
| 1+ | MTX | EMIT | 1 | — | 1.5 | — | 0 |
| 2+ | " | " | 2 | — | 4.0 | — | 0 |
| 3+ | " | " | 3 | — | 2.0 | — | 0 |
| 4+ | Hydro-cortisone | HPLC | 1 | — | 0 | — | 1.3 |
| 5+ | Hydro-cortisone | " | 2 | — | 0 | — | 1.9 |
| 6+ | Hydro-cortisone | " | 3 | — | 0 | — | 2.3 |

\# = Animal = Rabbit
\* = Microcapsule in pars plana
+ = Plaque in pars plana
RE = Right Eye
LE = Left Eye
AC = Anterior Chamber
PC = Posterior Chamber It is evident from the above results that biocompatible implants find effective use for treatment of a wide variety of ocular condutions. The implants provide for continuous administration of a drug over long periods of time, avoiding the need of a patient to administer drugs in much less effective ways, such as topically. In addition, treatments can be achieved by maintaining appropriately therapeutic levels of drugs in the eye, minimizing high concentrations throughout the host system which may have deleterious effects. The drug is retained in the appropriate site. Equilibration levels are rapidly achieved and maintained for long periods of time. Furthermore, one or only a few drug administrations may be required for treatments over extended periods of time, reducing the burden on the patient for self-administration, ensuring continued controlled medication, and minimizing the interference with the activities of the patient.

Polymeric encapsulation and/or incorporation protects doses of pharmacological agents from being diluted or degraded in the general circulation. The agents can be entrapped in various concentrations without any modifications. Encapsulation provides concentrated doses of medication which are more effective and less toxic than free drugs. Further, the drugs can be protected from enzymatic attack or immune recognition because polylactic acid is biocompatible and nontoxic.

The instant method provides an effective treatment for ocular diseases. The method is noninvasive in that it avoids injections into the interior of the eye yet is able to provide a therapeutically effective amount of agent to a diseased site.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for treating an eye condition which comprises:
    introducing into the suprachoroidal space an eye implant incapable of migration from the suprachoroid, said implant comprises from about 1 to about 80 weight % of an active agent selected from at least one of drugs, pharmaceutical agents, and bacterial agents in a pharmacologically acceptable biodegrable polymer which is degraded in the eye, wherein said implant provides an effective dosage of said drug over an extended period of time.

2. A method according to claim 1, wherein said implant in a plaque.

3. A method according to claim 2, wherein said plaque has length and width dimensions of about 0.5 to 10 mm×0.5 to 10 mm with a thickness of about 0.25 to 1. mm.

4. A method according to claim 1, wherein said bacterial agent is selected from acid-fast bacilli or *C. parvum*.

5. A method according to claim 1, wherein said polymer is a condensation polymer.

6. A method according to claim 5, wherein said polymer is a polyester.

7. A method according to claim 6, wherein said polyester comprises an hydroxyaliphatic carboxylic acid monomer.

* * * * *